(12) United States Patent
Feingold

(10) Patent No.: US 9,168,175 B2
(45) Date of Patent: Oct. 27, 2015

(54) METHOD FOR LASER CUTTING A CORNEAL POCKET

(76) Inventor: Vladimir Feingold, Laguna Niguel, CA (US)

( * ) Notice: Subject to any disclaimer, the term of this patent is extended or adjusted under 35 U.S.C. 154(b) by 0 days.

(21) Appl. No.: 13/222,042

(22) Filed: Aug. 31, 2011

(65) Prior Publication Data

US 2011/0319876 A1  Dec. 29, 2011

Related U.S. Application Data

(63) Continuation-in-part of application No. 12/281,749, filed on Sep. 4, 2008, now abandoned.

(51) Int. Cl.
*A61B 18/20* (2006.01)
*A61F 9/008* (2006.01)

(52) U.S. Cl.
CPC ... *A61F 9/00836* (2013.01); *A61F 2009/00872* (2013.01)

(58) Field of Classification Search
USPC .......................................................... 606/4, 5
See application file for complete search history.

(56) References Cited

U.S. PATENT DOCUMENTS

| | | | |
|---|---|---|---|
| 5,423,801 A | 6/1995 | Marshall et al. | |
| 5,993,438 A | 11/1999 | Juhasz et al. | |
| 6,106,553 A | 8/2000 | Feingold | |
| RE37,504 E | 1/2002 | Lin | |
| 6,543,453 B1 | 4/2003 | Klima et al. | |
| 6,551,307 B2 | 4/2003 | Peyman | |
| 6,599,305 B1 | 7/2003 | Feingold | |
| 6,755,859 B2 | 6/2004 | Hoffmann et al. | |
| 6,768,576 B2 | 7/2004 | Caudle | |
| 6,827,738 B2 | 12/2004 | Willis et al. | |
| 7,008,447 B2 | 3/2006 | Koziol | |
| 7,101,364 B2 | 9/2006 | Bille | |
| 7,455,691 B2 | 11/2008 | Feingold | |
| 8,171,937 B2 | 5/2012 | Bendett et al. | |
| 2001/0027314 A1 | 10/2001 | Peyman | |
| 2003/0014042 A1* | 1/2003 | Juhasz et al. | 606/5 |
| 2004/0085511 A1 | 5/2004 | Uno et al. | |
| 2004/0243112 A1* | 12/2004 | Bendett et al. | 606/5 |
| 2005/0046794 A1 | 3/2005 | Silvestrini et al. | |
| 2007/0219542 A1* | 9/2007 | Yahagi | 606/5 |
| 2008/0287935 A1 | 11/2008 | Bille | |
| 2009/0137988 A1* | 5/2009 | Kurtz | 606/4 |
| 2009/0198325 A1 | 8/2009 | Holliday et al. | |
| 2010/0087802 A1 | 4/2010 | Bischoff et al. | |

OTHER PUBLICATIONS

International Search Report and the Written Opinion of the International Searching Authority for PCT/US2012/052645 filed Aug. 28, 2012.

\* cited by examiner

*Primary Examiner* — William Thomson
*Assistant Examiner* — Jeffrey Lipitz
(74) *Attorney, Agent, or Firm* — Andres F. Arrubla; Victor Siber

(57) ABSTRACT

A method for using a laser to create a pocket in a patient's cornea is provided. The pocket is created using a femtosecond or a nanosecond laser. The laser ablates tissue within the cornea in a specific shape. The shape of the pocket can be determined by software to custom program a three-dimensional path of the laser. A variety of corneal pocket configurations or computer programmed shapes can be used accommodate various corneal lens shapes and sizes. An intracorneal lens can then be inserted into the pocket, in order to correct the patient's vision.

4 Claims, 7 Drawing Sheets

METHOD FOR LASER CUTTING A CORNEAL POCKET

CROSS REFERENCE TO RELATED APPLICATION

This application claims priority to earlier filed U.S. patent application Ser. No. 12/281,749, filed on Jan. 8, 2009, the disclosure of which is hereby incorporated by reference, in its entirety.

FIELD OF THE INVENTION

The present invention relates generally to ocular surgery. More particularly, the present invention relates to a method for laser cutting a corneal pocket.

BACKGROUND OF THE INVENTION

Presbyopia is the gradual loss of near vision, which often accompanies the aging process. The eyes of a person suffering from presbyopia have a diminished ability to focus on near objects such as books, magazines, or a computer screen. Symptoms of presbyopia can include difficulty reading fine print and blurred vision when transitioning the focus of the eye between near and distant objects.

There are several common treatments for presbyopia. A dedicated pair of reading glasses is one such treatment. Reading glasses provide magnification of near objects to provide for improved vision. However, if a person also needs glasses to focus on distant objects switching between reading glasses and distance glasses can be inconvenient. Another treatment is bifocal glasses, which provide a portion of the glasses lens for assisting with distance vision and a portion for assisting with near vision. While bifocals provide a single pair of glasses for both near and distance vision correction, they can cause disorientation. Contact lenses for the surface of the eye have also been developed which provide vision correction for both near and distance vision. Although these treatments provide vision correction for a person suffering from presbyopia, each requires at least one an additional accessory or pair of contact lenses that must be worn or used daily. Additionally, very small lenses for insertion into the eye are being developed. However, a small pocket must be made in the cornea into which the lens can be inserted.

Accordingly, it is desirable to provide method for creating such a small pocket in the cornea into which the lens can be inserted.

SUMMARY OF THE INVENTION

The foregoing needs are met, to a great extent, by the present invention, wherein in one aspect an apparatus is provided that in some embodiments includes a method for laser cutting a corneal pocket into which a lens can be inserted.

In accordance with one aspect of the present invention, a method for creating a corneal pocket includes providing a low-energy femtosecond or nanosecond laser configured to create a corneal pocket. The method can also include positioning the laser proximate to a cornea such that it can be used to create the corneal pocket and determining a movement path for the laser, in order to form the corneal pocket having a specific pocket shape wherein the movement path follows a generally curvilinear path. Additionally, the method can include focusing a laser beam from the laser to a predetermined depth within the cornea between an anterior surface and a posterior surface of the cornea such that the laser beam cut corneal tissue at the predetermined depth. The method can also include moving the laser beam in the movement path in order to create the corneal pocket having the specific pocket shape.

In accordance with another aspect of the present invention, the method can include moving the laser toward the middle of the cornea to compensate for astigmatic effect. The method can also include using a laser with an energy output in a range between approximately 0.2 microjoules and 1.5 microjoules. The laser can also have a spot size in a range of approximately 0.2 to 4.0 microns and the corneal pocket can be positioned at a depth in a range of approximately 220 microns to 350 microns. Additionally, the laser with multiple laser beam spots and the space between the spots can be eliminated. The method can further include programming the laser to create the specific pocket shape.

In accordance with still another embodiment of the present invention a method for creating a corneal pocket includes providing a low-energy femtosecond or nanosecond laser configured to create a corneal pocket. The method can also include positioning the laser proximate to a cornea such that it can be used to create the corneal pocket and determining a movement path for the laser, in order to form the corneal pocket having a specific pocket shape wherein the movement path follows a generally curvilinear path. The method can include using positioning software in order to create the specific shape. Additionally, the method can include focusing a laser beam from the laser to a predetermined depth within the cornea between an anterior surface and a posterior surface of the cornea such that the laser beam cuts and separates corneal tissue at the predetermined depth. The method can also include moving the laser beam in the movement path in order to create the corneal pocket having the specific pocket shape.

In accordance with still another embodiment of the present invention a method for creating a corneal pocket includes providing a low-energy femtosecond or nanosecond laser configured to create a corneal pocket. The method can also include positioning the laser proximate to a cornea such that it can be used to create the corneal pocket and determining a three-dimensional movement path for the laser, in order to form the corneal pocket having a specific pocket shape wherein the movement path follows a generally curvilinear path. The method can include programming a computer to control the laser such that it follows the three-dimensional movement path to form the specific shape. Additionally, the method can include focusing a laser beam from the laser to a predetermined depth within the cornea between an anterior surface and a posterior surface of the cornea such that the laser beam cuts and separates corneal tissue at the predetermined depth. The method can also include moving the laser beam in the movement path in order to create the corneal pocket having the specific pocket shape.

In accordance with another aspect of the present invention, the method can include moving the laser toward the middle of the cornea to compensate for astigmatic effect. The method can also include using a laser with an energy output in a range between approximately 0.2 microjoules and 1.5 microjoules. The laser can also have a spot size in a range of approximately 0.2 to 4.0 microns and the corneal pocket can be positioned at a depth in a range of approximately 220 microns to 350 microns. Additionally, the laser can have multiple laser beam spots and the space between the spots can be eliminated.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
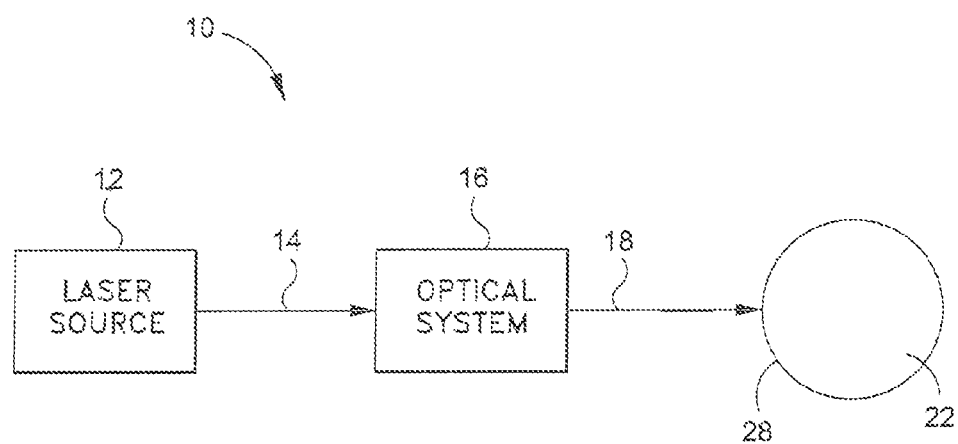
FIG. 1 illustrates a laser surgery apparatus for laser surgery to create an intracorneal pocket in accordance with an embodiment of the invention.

The invention will now be described with reference to the drawing figures, in which like reference numerals refer to like parts throughout. An embodiment in accordance with the present invention provides an apparatus and method for creating a flap or pocket in the cornea. This lens or pocket preferably is created by a laser used in conventional lasik surgery.

FIG. 1 illustrates a laser surgery apparatus 10 for laser surgery to create an intracorneal pocket in accordance with an embodiment of the invention. The laser surgery apparatus 10 can include a laser source 12 which can generate and control, using software, a source beam 14 having a continuous train of laser pulses of substantially constant pulse duration and pulse energy. In one embodiment of the laser surgery apparatus 10, a source beam 14 can take the form of a femtosecond or a nanosecond laser. The source beam 14 can also have a wavelength greater than 800 nanometers and a pulse energy in a range of approximately 0.2 mu.J. to 1.5 mu.J. Using less energy for the pulse is preferable, but can be any level of energy suitable for creating the corneal pocket.

The laser surgery apparatus 10 further includes an optical system 16 for forming a shaped laser beam 18 and directing the shaped laser beam 18 toward and into the cornea 28 of an eye 22. The laser beam 18 can be programmed with a computer to determine the path of the laser beam 18 over the patient's eye. Additionally, the laser beam 18 can be configured to follow a three-dimensional path to cut and separate the cornea to form a pocket for the insertion of the lens.

Figure 2:
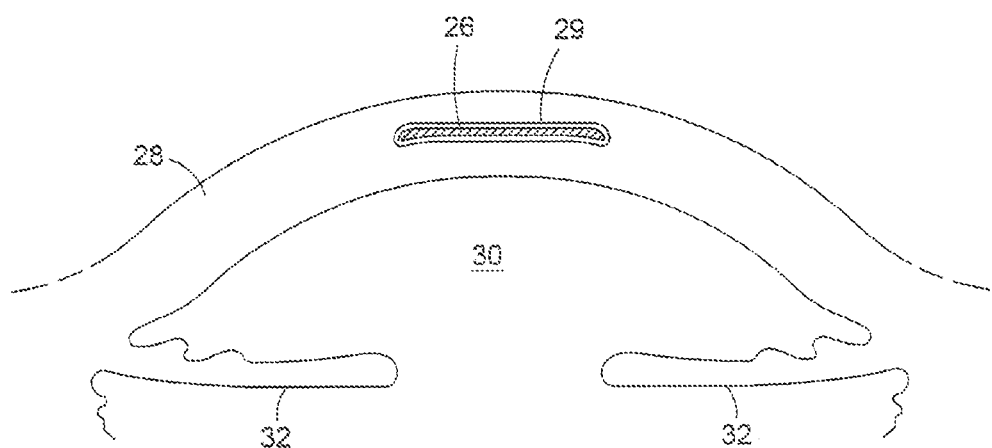
FIG. 2 is a sectional view of the anterior portion of the eye having an intracorneal lens disposed therein, according to an embodiment of the invention.

FIG. 2 is a sectional view of the anterior portion of the eye 22 having an intracorneal lens 26 disposed therein, according to an embodiment of the invention. In the embodiment of the invention shown in FIG. 2, intracorneal lens 26 may be disposed within a cornea 28 of the eye 22, which may partially enclose the anterior chamber 30 of the eye 22. Also shown in FIG. 2 is an iris 32. In accordance with an embodiment of the invention, lens 26 may be inserted within cornea 28 following formation of a corneal pocket 29, which may be formed using a laser surgery apparatus 10 as shown in FIG. 1.

Intracorneal lens 26 is not restricted to the configuration shown in the drawings, but may have various shapes, such as circular or oval. In some embodiments, intracorneal lens 26 may have a doughnut-like configuration. The size and shape of intracorneal lens 26 may, in some cases, determine the size and shape of the corneal pocket.

The intracorneal lens 26 preferably may be formed of a biocompatible material that permits sufficient gas diffusion to allow adequate oxygenation of internal eye tissues. Such materials may include silicone, hydrogels, urethanes or acrylics. It also may be desirable that the lens be made of a hydrophilic material which swells somewhat when hydrated. Such materials, for example, hydrogels, are well known and are used in some present contact lenses.

The optical characteristics of intracorneal lens 26 may be selected for correcting various visual deficiencies, including without limitation: myopia (short sightedness), hypermetropia (long sightedness), presbyopia and astigmatism. As an example, intracorneal lens 26 may have a diopter power or value in the range of from +15 to −30. Intracorneal lens 26 may be customized for a particular patient to provide optical characteristics to correct a specific visual defect of a patient. Intracorneal lens 26 may be multi-focal, may be provided as an off-the-shelf unit with pre-determined optical characteristics and may have zones with optical power and zones without optical power. It is to be understood that the present invention is not limited to treatment of the aforementioned visual defects, and that treatment of other eye conditions is also within the scope of the invention.

Figure 3:
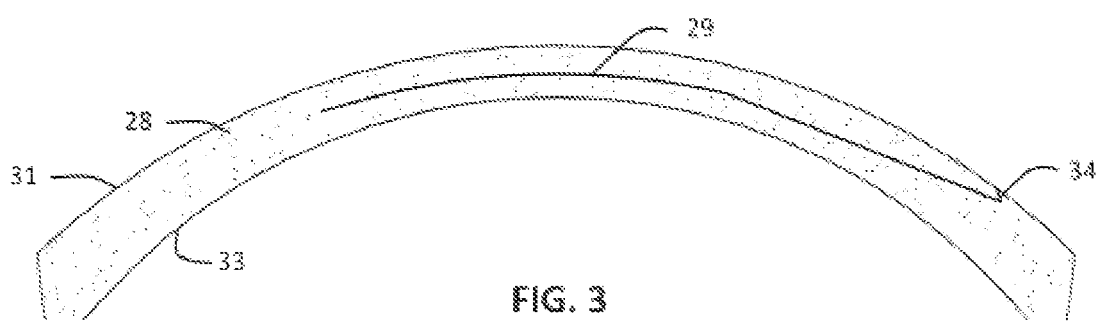
FIG. 3 illustrates a sectional view of the anterior portion of an eye having an implant disposed within the cornea of the eye according to an embodiment of the invention.

FIG. 3 shows a cross section of a cornea 28 having a corneal pocket 29 formed by a laser surgery apparatus 10 in accordance with one embodiment of the invention. Cornea 28 has an anterior surface 31 and a posterior surface 33. Corneal pocket 29 may be formed by photo disruption using laser beam 18 from a laser source 12.

The corneal pocket 29 may be formed with a thickness and shape that conforms to the surfaces of the intracorneal lens 26. For example, the interior surfaces of the corneal pocket 29 may be convex, concave, planar or irregular. The edges of the corneal pocket 29 may form an outline having various shapes depending on the desired outcome and the shape of the intracorneal lens 26. The various configurations of corneal pockets can be adapted to be used with lenses of various shapes and sizes. The corneal pocket can also be configured to facilitate the insertion of the lens and minimize the size of the incision for improved post-surgical healing of the cornea. The corneal pocket can also include an entry channel 34 that may be cut into the cornea 28 after the corneal pocket 29 is formed. Entry channel 34 may permit the insertion of the intracorneal lens 26 into the corneal pocket 29.

Figure 4:
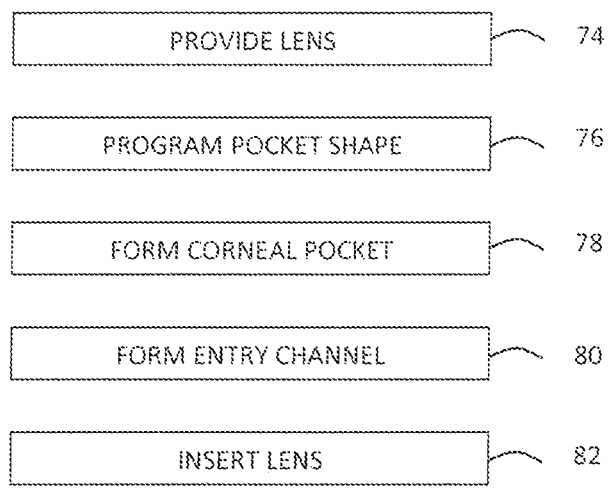
FIG. 4 illustrates a series of steps involved in a method for inserting a lens into the cornea of the patient.

FIG. 4 schematically represents a series of steps involved in a process for creating a corneal pocket and inserting a lens in the cornea of a patient, according to one embodiment of the invention. The process may begin with the step 74 of providing an intracorneal lens 26. The intracorneal lens 26 may or may not have optical power depending on the purpose of the intracorneal lens 26. In step 78 a corneal pocket 29 may be formed. This may be done using the laser surgery apparatus 10 shown in FIG. 1. In particular, a laser source 12 being controlled by an optical system 16 may be used to focus a laser beam 18 within the corneal tissue. The laser beam 18 will cut and separate a region of the cornea tissue in the area of the focus of the laser beam 18. The focus of the laser beam 18 may then be moved laterally by hand to cut a layer of corneal tissue. While the focus of the laser beam 18 is being moved laterally, it may be maintained a fixed depth within the cornea using known laser surgical techniques. The focus of the laser beam 18 may be easily, quickly and accurately moved laterally by controlled software within the confines of the pocket region without the risk of cutting outside the desired area defined by the software.

The thickness of the corneal pocket created using the above techniques will be about the size of the diameter of the laser beam 18 focal point. In some cases, depending on the thickness and shape of the intracorneal lens 26, additional tissue may be cut at different depths within the cornea 28.

In step 80 an entry channel 34 may be formed. This may be accomplished using the laser source 12 or may be formed using a conventional scalpel. Entry channel 34 may provide a means for insertion of the intracorneal lens 26 and also will allow the release of gasses created by laser ablation when the intracorneal pocket 29 is formed.

The intracorneal lens 26 may then be inserted into the intracorneal pocket 29 in step 82. Step 82 may further involve temporarily deforming the intracorneal lens 26 before it is introduced into the cornea 28. The intracorneal lens 26 may be deformed by rolling, folding, and the like. The intracorneal lens 26 may have prescribed memory characteristics that allow it to return to its original size and configuration after insertion into the cornea 28, while retaining its desired optical characteristics. The intracorneal lens 29 may be made of a hydrophilic material which swells when hydrated. The lens may be inserted fully hydrated to elastically fit into a corneal pocket, or while at least partly dehydrated such that subsequent hydration helps secure the fit in the pocket.

Figure 5A:
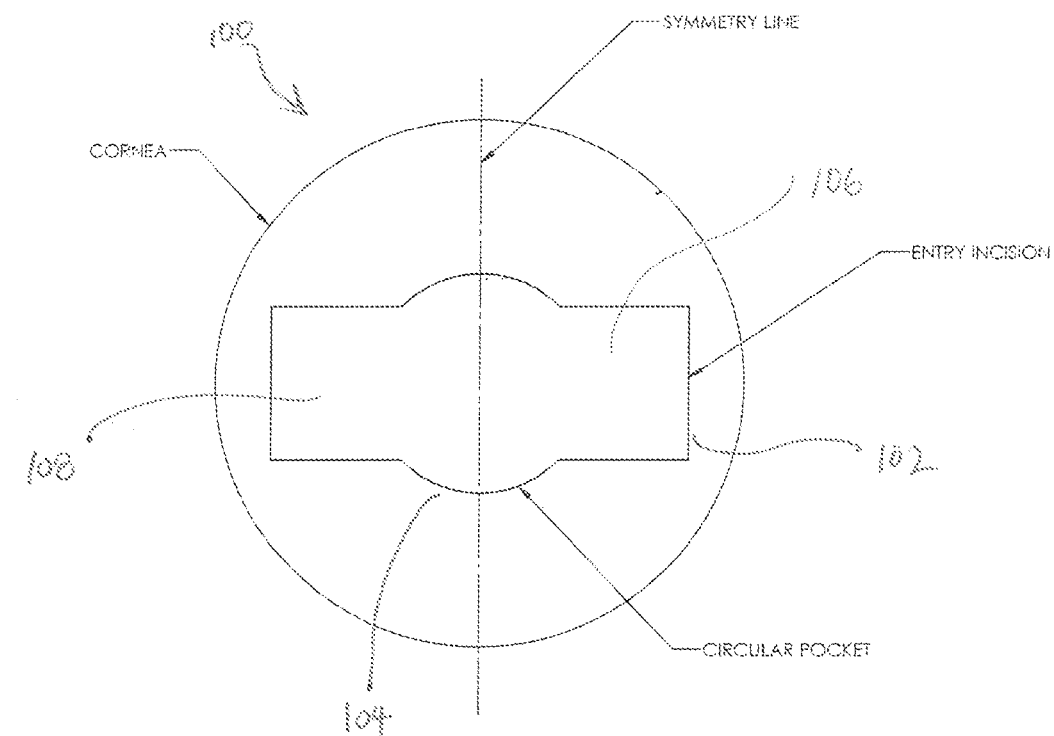
FIGS. 5A and 5B illustrate incisions in a cornea and a corneal pocket in accordance with an embodiment of the invention.
Figure 5B:
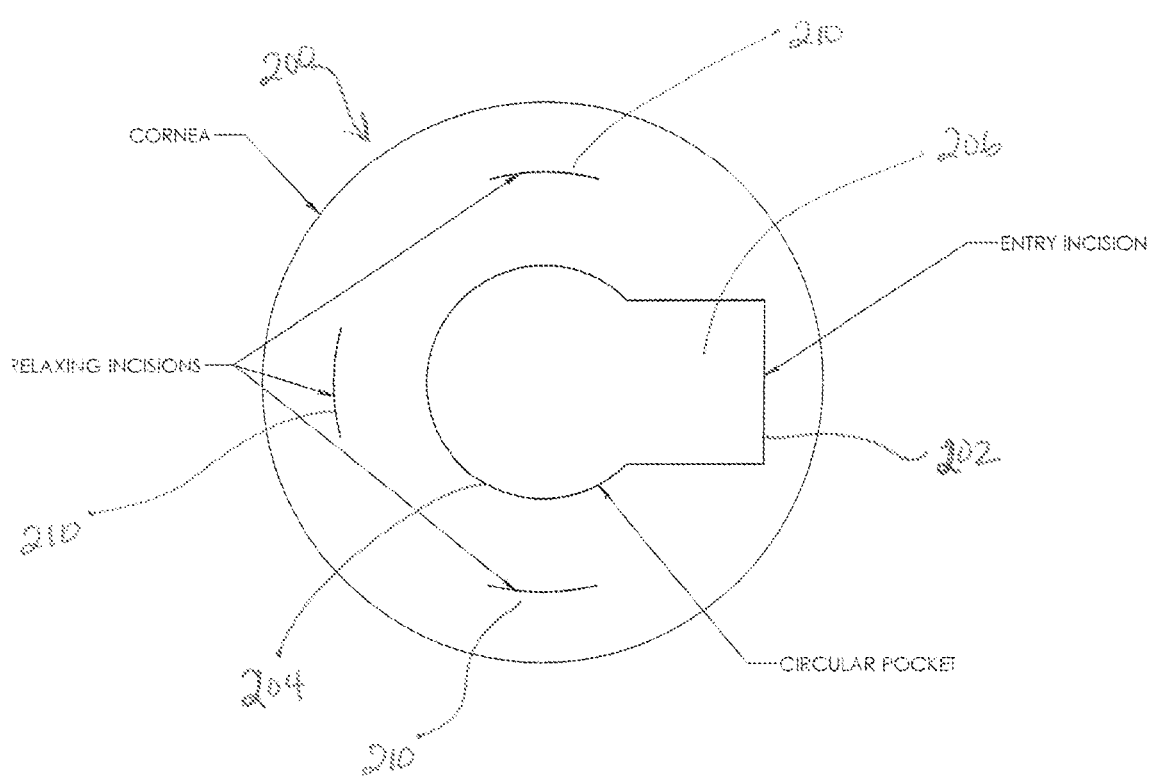

FIGS. 5A and 5B illustrate incision patterns in a cornea, in accordance with an embodiment of the invention. As illustrated in FIGS. 5A and 5B, an entry incision 102, 202 can be made on the cornea 100, 200. The entry incision 102, 202 is shown as being positioned on a rightward edge of the cornea 100, 200, in FIGS. 5A and 5B. However, the entry incision 102, 202 can be positioned in any suitable portion of the cornea 100, 200. A circular pocket 104, 204 can also be formed in the cornea. An insertion tunnel 106, 206 can be positioned between the entry incision 102 and the pocket 104. Additionally, as illustrated in FIG. 5A, a second tunnel 108 can be positioned to the left of the circular pocket 104. Alternately, as shown in FIG. 5B, relaxing incisions 210 can be made in the cornea 200, in order to ease the insertion of the corneal lens and reduce astigmatism.

Figure 6A:
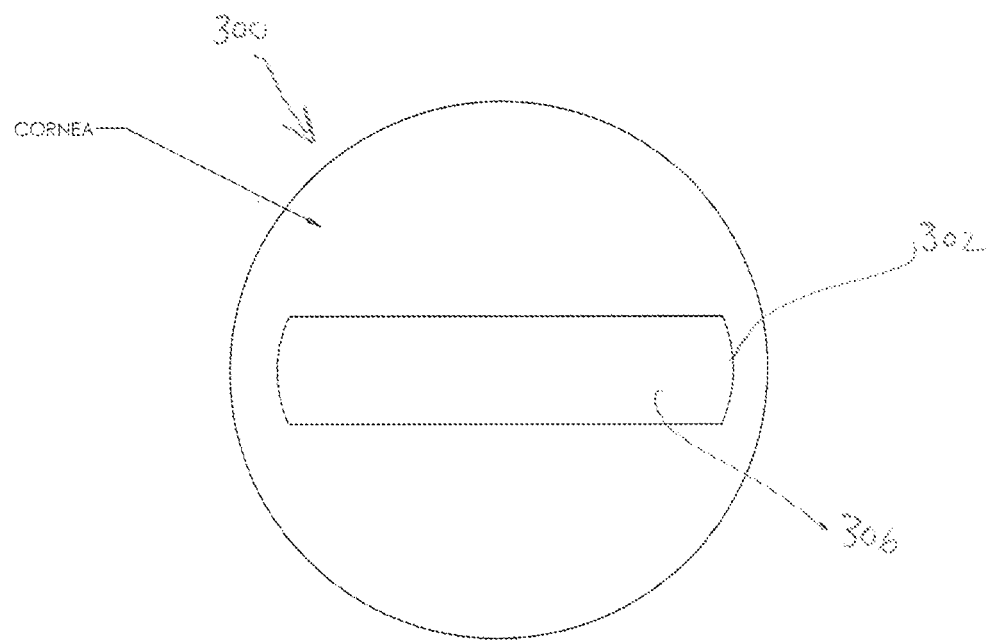
FIGS. 6A and 6B illustrate incisions in a cornea in accordance with an embodiment of the invention.
Figure 6B:
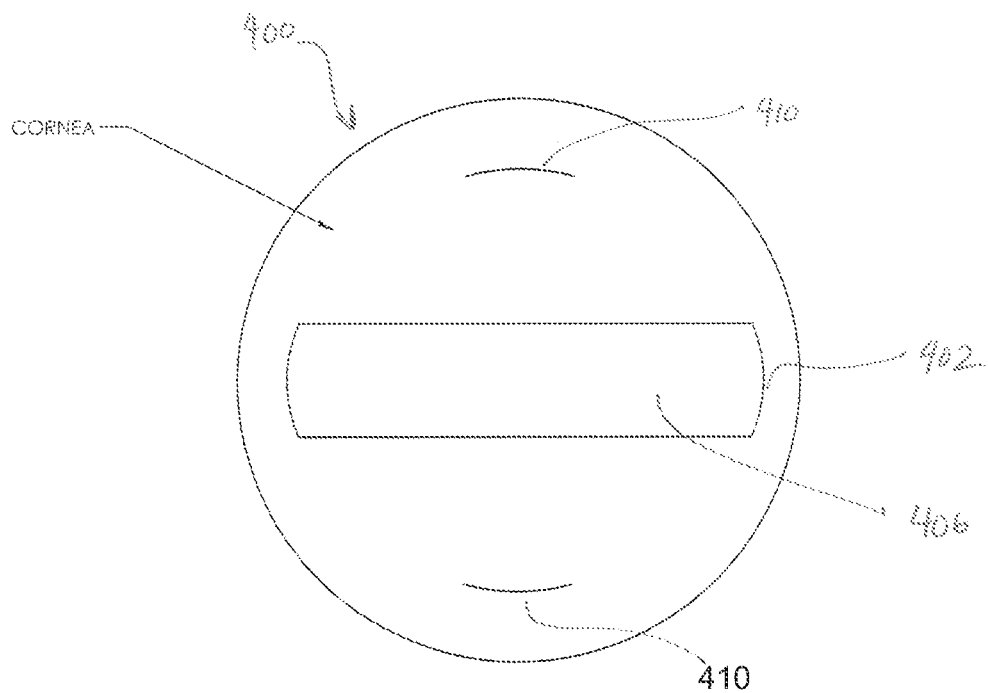

FIGS. 6A and 6B also illustrate incision patterns in a cornea, in accordance with an embodiment of the invention. As illustrated in FIGS. 6A and 6B, an entry incision 302, 402 can be made on the cornea 300, 400. The entry incision 302, 402 is shown as being positioned on a rightward edge of the cornea 300, 400, in FIGS. 6A and 6B. However, the entry incision 302, 402 can be positioned in any suitable portion of the cornea 300, 400. An insertion tunnel 306, 406 can be positioned leftward of the entry incision 302, 402, and can extend across the cornea 300, 400. Additionally, as shown in FIG. 6B, relaxing incisions 410 can be made in the cornea 400, in order to ease the insertion of the corneal lens and reduce a preexisting astigmatism.

Figure 7:
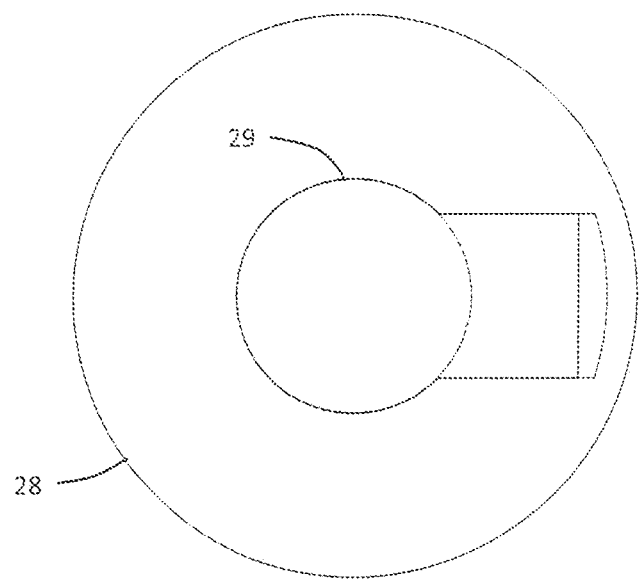
FIG. 7 illustrates a top down view of a corneal pocket in accordance with an embodiment of the invention.

FIG. 7 illustrates a top down view of the same corneal pocket 29. The pocket and the relaxing incisions can be made with a femtosecond or nanosecond laser having an energy profile in a range of approximately 0.2 microjoules to 1.5 microjoules. Any suitable energy level can be used, however lower energy output is preferable. Additionally, the laser beam can have a spot size in a range of approximately 0.2 microns to 4.0 microns. The depth of the cut can be in a range of approximately 220 microns to 350 microns. It should be noted that if the cut is too deep the structure of the cornea can become less stable. The pocket profile 29 shown in FIG. 8 can be used to minimize distortion of the patient's vision through the newly implanted lens. However, if the patient suffers from astigmatism the cut can be moved toward the middle of the cornea in order to minimize the astigmatic effect.

Figure 8A:
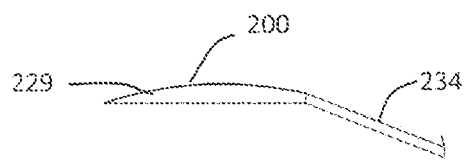
FIGS. 8A and 8B illustrate a 3 dimensional path for the laser beam in accordance with an embodiment of the invention.
Figure 8B:
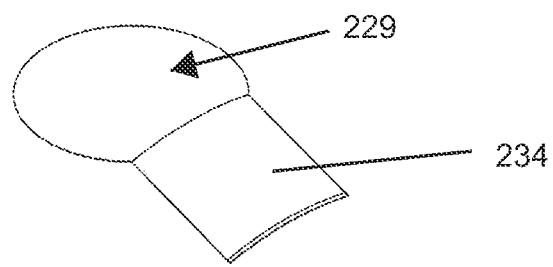
Figure 9:
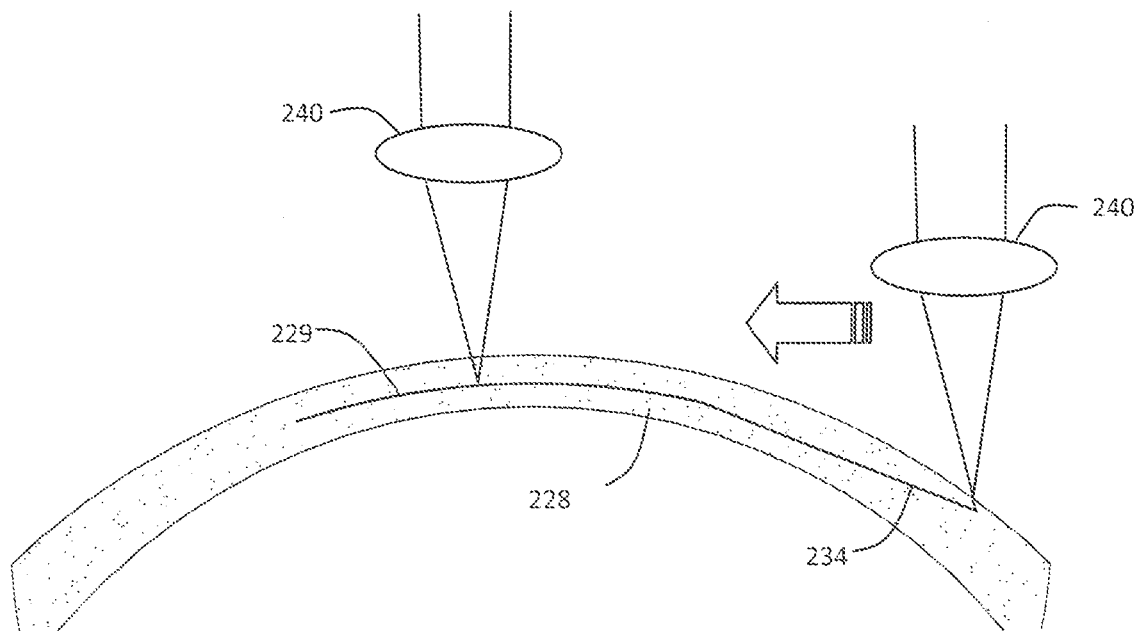
FIG. 9 illustrates a path for movement of the laser beam in accordance with an embodiment of the invention.

FIGS. 8A, 8B, and 9 illustrates a path for the laser beam and a direction for the movement of the laser beam, in accordance with an embodiment of the invention. More particularly, FIG. 8A illustrates a side view of the path for the laser beam and FIG. 8B illustrates a top down view of the path The pocket 229 can be formed and an adjacent entry channel 234 can be formed in order to allow the insertion of the intracorneal lens into the corneal pocket 229. While FIGS. 8A and 8B illustrate a path for the laser beam, this is simply one example of the path that can be used to form the pocket 229 and the entry channel 234. Any path that is suitable for the purpose of forming a pocket can be used. Preferably, the path the laser is moved in is curvilinear to follow the natural curvature of the eye. FIG. 9 illustrates the laser beam 240 moving across an axis of the eye. The laser beam 240 can have a single beam or multiple beams creating a single laser spot or multiple laser spots respectively. Additionally, if the laser beam used has multiple spots, preferably there is no space between the spots of the laser beam.

As can be appreciated by those skilled in the art, the present invention may provide a method for correcting the vision of a patient with an intracorneal lens 26 that may be easily inserted into a corneal pocket 29. The corneal pocket 29 may be created using a laser source 12 or may be created using other forms of electromagnetic radiation. The creation of the corneal pocket 29 is facilitated by the use of software that prevents the laser beam 18 from cutting and separating tissue outside the boundary of a desired shape. A variety of corneal pocket configurations may be used to accommodate various corneal lens shapes and sizes. Other surgical procedures, such as arcuate cuts, may also be made using the techniques of the invention.

The many features and advantages of the invention are apparent from the detailed specification, and thus, it is intended by the appended claims to cover all such features and advantages of the invention, which fall within the true spirit, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for creating a corneal pocket and an entry channel for inserting and positioning an intracorneal lens in the corneal pocket, the method comprising:
   providing a low-energy nanosecond laser configured to create the corneal pocket;
   positioning the laser proximate to a cornea such that it can be used to create the corneal pocket;
   determining a generally curvilinear movement path and an energy output in a range between approximately 0.2 microjoules and 1.5 microjoules for the laser in order to form the corneal pocket having a specific shape and a thickness conforming to predefined surfaces of an intracorneal lens to be inserted into the corneal pocket;
   configuring the laser to follow the generally curvilinear movement path using a positioning software;
   focusing a laser beam from the laser to a focal point at a predetermined depth within the cornea between an anterior surface and a posterior surface of the cornea such that the laser beam cuts and separates corneal tissue at the predetermined depth;
   moving the laser beam in the generally curvilinear movement path in order to create the corneal pocket having the specific shape and a thickness about the size of a diameter of the laser beam focal point;
   forming the entry channel into the corneal pocket with the laser beam, wherein the entry channel is at an obtuse angle from the corneal pocket toward an entry incision on the cornea; and
   forming at least one arc shaped relaxing incision(s), using an energy output that is less than the determined energy output used to create the corneal pocket, in a region of the cornea at a depth in the range of 220 microns and 350 microns and outside of the corneal pocket and the entry channel used to correct a preexisting astigmatism.

2. The method of claim 1, further comprising using a laser with a spot size in a range of approximately 0.2 to 4.0 microns.

3. The method of claim 1, further comprising providing a laser with multiple laser beam spots.

4. The method of claim 3, further comprising eliminating space between the laser beam spots.

* * * * *